(12) United States Patent
Clark

(10) Patent No.: US 7,862,619 B2
(45) Date of Patent: Jan. 4, 2011

(54) KNEE JOINT PROSTHESIS

(75) Inventor: Ron Clark, Valparaiso, IN (US)

(73) Assignee: VOT, LLC, Warsaw, IN (US)

( * ) Notice: Subject to any disclaimer, the term of this patent is extended or adjusted under 35 U.S.C. 154(b) by 457 days.

(21) Appl. No.: 11/197,059

(22) Filed: Aug. 5, 2005

(65) Prior Publication Data

US 2007/0032876 A1 Feb. 8, 2007

(51) Int. Cl.
*A61F 2/38* (2006.01)
(52) U.S. Cl. ............ 623/20.3; 623/20.34; 623/20.36; 623/23.19
(58) Field of Classification Search ............... 623/20.3, 623/20.31, 23.19, 20.34, 20.36
See application file for complete search history.

(56) References Cited

U.S. PATENT DOCUMENTS

| | | | |
|---|---|---|---|
| 3,852,830 A | | 12/1974 | Marmor |
| 4,034,418 A | * | 7/1977 | Jackson et al. ............. 623/20.3 |
| 4,274,163 A | * | 6/1981 | Malcom et al. ............. 606/94 |
| 4,744,754 A | * | 5/1988 | Ross .......................... 433/173 |
| 5,019,103 A | * | 5/1991 | Van Zile et al. ........... 623/20.34 |
| 5,116,377 A | * | 5/1992 | Skripitz et al. ............ 623/23.19 |
| 5,171,276 A | | 12/1992 | Caspari |
| 5,201,768 A | | 4/1993 | Caspari |
| 5,207,711 A | | 5/1993 | Caspari |
| 5,336,266 A | * | 8/1994 | Caspari et al. ............ 623/20.35 |
| 5,376,123 A | * | 12/1994 | Klaue et al. ............... 623/23.19 |
| 5,702,446 A | * | 12/1997 | Schenck et al. ........... 623/23.55 |
| 5,931,870 A | | 8/1999 | Cuckler |
| 2002/0082703 A1 | | 6/2002 | Repicci |
| 2005/0015153 A1 | | 1/2005 | Goble |

* cited by examiner

*Primary Examiner*—Bruce E Snow
(74) *Attorney, Agent, or Firm*—John W. Boger; Heslin Rothenberg Farley & Mesiti P.C.

(57) ABSTRACT

The present invention relates to a knee joint prosthesis including femoral and tibial components. The bodies of the components possess a network of channels which may be used to deliver bone cement to the component bone interface after the components are implanted. The body of the femoral component possesses a network of channels which is in communication with a bore on the distal surface of the component which may be used to deliver bone cement into the network of channels after the component is implanted. The body of the tibial component possesses a network of channels which is in communication with a bore on the proximal surface of the component which may be used to deliver bone cement into the network of channels after the component is implanted. The components are suitable for implantation using arthroscopic as well as open surgical procedures. The components may be used as unicondylar implants in either compartment of the knee or in both compartments of the knee.

26 Claims, 9 Drawing Sheets

KNEE JOINT PROSTHESIS

BACKGROUND OF THE INVENTION

1. Field of the Invention

The present invention relates to prosthetic implants and, more particularly, to prostheses for human knee joints that are implantable by means of arthroscopic as well as open surgical techniques.

2. Description of Related Art

It is common to provide implants to resurface worn articular surfaces of knees. Many of the prior art prostheses require large incisions to gain adequate access to the joint space to perform the surgery and the removal of a great deal of bone from the femur and tibia in order to accommodate the implant, thereby causing large amounts of surgical trauma to the patients and reducing the amount of bone available in the event that revision surgery is required. In addition, the removal of too much bone may lead to failure of the implanted prosthesis due to subsidence of the implant into the underlying bone necessitating revision surgery to replace the failed implants.

Bone cement is typically used to secure implant components. Misalignment of components may occur when bone cement is placed on the prepared bone surface before the components are implanted into position. When a component is implanted into bone cement which has been placed on the prepared bone surface, bone cement may escape from between the bone and the edges of the implant. When bone cement is injected into a portal located on a side wall of an implant, bone cement may leak from the portal into the joint space. If left in the joint space, such excess or leaked bone cement may cause irritation. On the other hand, inadequate amounts of bone cement may result in inadequate fixation resulting in the loosening of the implant.

BRIEF SUMMARY OF THE INVENTION

Accordingly, it is a primary object of the present invention to overcome the above mentioned disadvantages associated with prior art devices and surgical procedures.

Another object of the present invention is to reduce surgical trauma by providing prosthetic implants that reduce the required size of surgical incisions and that reduce the amount of bone that must be removed during surgery when compared to prior art devices and surgical procedures.

Another object of the present invention is to reduce the leakage of bone cement into the joint space by providing an improved system for delivering bone cement to the interface between the implant and the bone.

Another object of the present invention is to reduce the likelihood of subsidence of implants by providing implants that require a minimal resection of bone such that the bone architecture is left intact and better able to adequately support the implants.

Another object of the present invention is to provide an implant that, in the event that revision surgery is required, would allow the use of a standard unicompartment replacement knee prosthesis in the revision surgery by providing implants that require a minimal resection of bone such that the bone architecture is left intact leaving more bone stock available for use in revision surgery when compared to prior art devices and surgical procedures.

A knee joint prosthesis including femoral and tibial components is disclosed. The body of the femoral component possesses a network of bores which have openings in the proximal surface of the femoral component. The network of bores communicates with an opening formed on the distal surface of the component. The network of bores may be used to deliver bone cement to the implant and bone interface after the implant has been placed in the end of the prepared femur. The body of the tibial component has an internal network of bores in communication with channels or openings formed on the distal surface of the tibial component. The network of bores communicates with an opening formed on the proximal surface of the tibial component. The network of bores may be used to deliver bone cement to the implant and bone interface after the implant has been place in the end of the prepared femur. In another embodiment of the invention, the body of the femoral component possesses a network of bores which is in communication with the bore of a cannulated fastener that attaches the femoral component to a femur. The tibial component possesses a network of grooves formed upon its distal surface which is in communication with a central bore within a post on the distal surface of the tibial component. A cannulated fastener is attached to the post on the distal surface of the tibial component to attach the tibial component to the tibia.

DETAILED DESCRIPTION OF THE INVENTION

The present invention relates to prosthetic implants and, more particularly, to prostheses for human knee joints that are implantable by means of arthroscopic as well as open surgical techniques.

The femoral component 10 of the prosthesis of the present invention is illustrated in FIG. 1-5.

Figure 1:
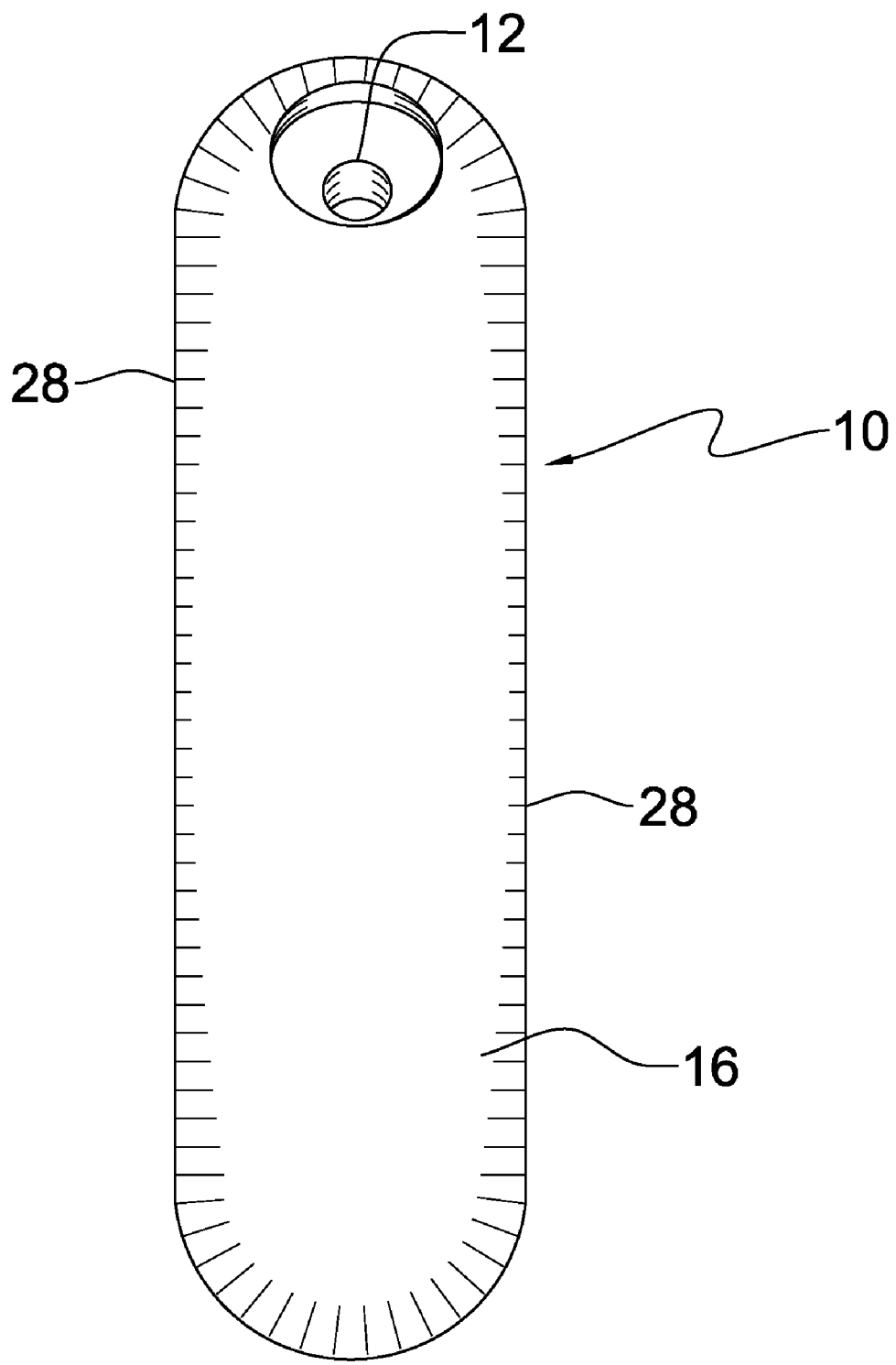
FIG. 1 is a view of the distal surface of the femoral component of the present invention.

A distal view of the femoral component 10 is shown in FIG. 1. The femoral component 10 may have one or more through holes 12 passing through the distal surface of 16 of the femoral component 10 for receiving a bone screw or other fastener known in the art for attaching the femoral implant 10 to the distal end of a femur. The periphery 28 of the femoral component is continuous, smooth and unbroken by any openings.

Figure 2:
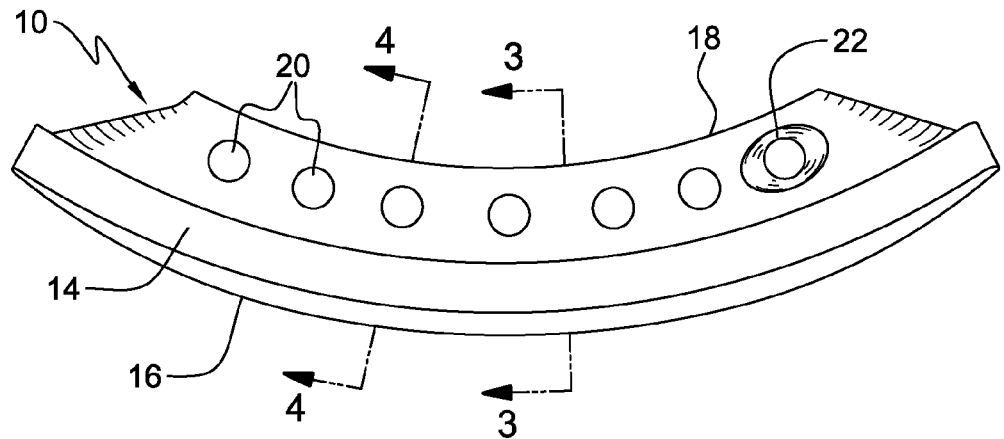
FIG. 2 is a side elevational view of the femoral component of FIG. 1.

As shown in FIG. 2, the femoral component 10 comprises a curved body portion 14 having a convexly curved distal surface 16 and a concave proximal surface 18. A plurality of generally transverse bores or holes 20 are formed through the body portion 14 substantially perpendicular to the longitudinal axis of the femoral component. The inner surface 22 of one or more of the transverse bores 20 may be internally threaded or otherwise adapted to receive and attach to the distal end of a fastener. A generally longitudinally oriented bore (not shown) passes through the body portion 14 of the femoral component 10 substantially perpendicular to the transverse bores 20 intersecting the transverse bores 20 causing the transverse bores 20 to be in communication with each other forming an interconnecting network of channels.

Figure 3:
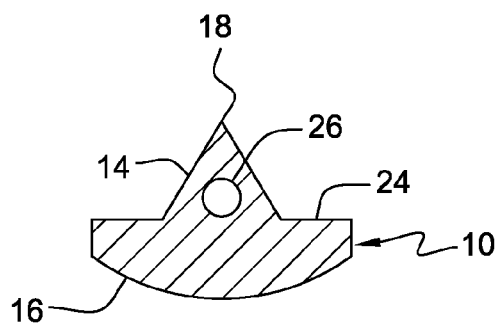
FIG. 3 is a cross-sectional view of the femoral component taken along section 3-3 of FIG. 2
Figure 6:
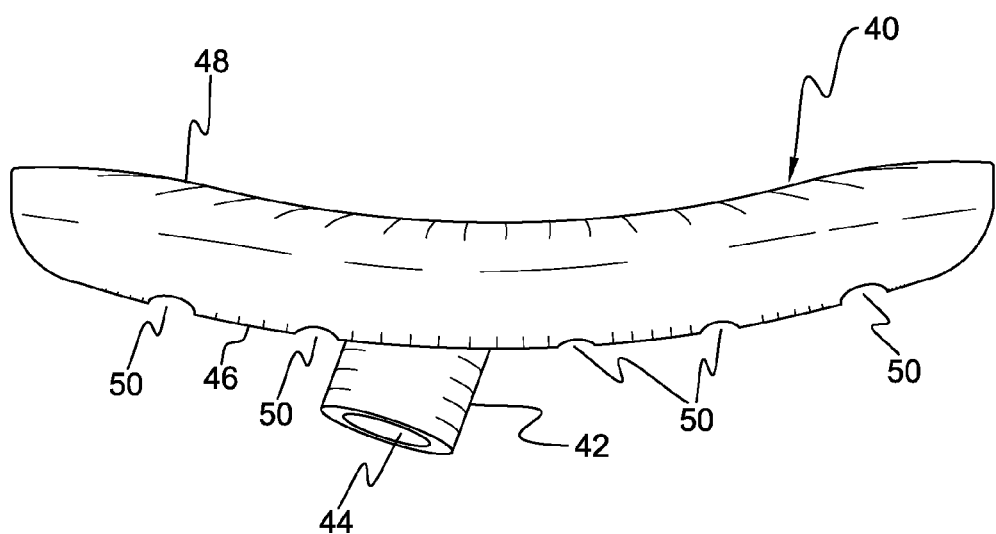
FIG. 6 is a side elevational view of the tibial component of the present invention.

FIG. 3 shows a cross-sectional view of the body 14 of the femoral implant 10 taken along the line III-III in FIG. 2. The femoral implant 10 includes a distal surface 16 configured for contacting the proximal surface 48 of a tibial implant 40 which is shown in FIG. 6. The femoral implant 10 may also include an apex portion 18 and support shoulders 24 to engage the prepared distal end of the femur. The apex 18 is shown to be triangular in cross-section, but it may be rounded, squared, or other geometric shape. The apex portion 18 may be configured to be received in the cancellous bone material of the femur, whereas the supports 24 may be configured to contact the cortical bone material of the femur, so that load sharing between the cortical bone and the cancellous bone may be accomplished. The body 14 contains a portion of the central bore 26 which intersects the transverse bores 20 causing the transverse bores 20 to be in communication with each other forming an interconnecting network of channels.

Figure 4:
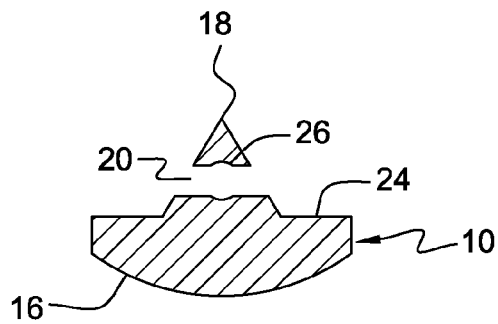
FIG. 4 is a cross-sectional view of the femoral component taken along section 4-4 of FIG. 2.

FIG. 4 shows a cross-sectional view of the body 14 of the femoral implant 10 taken along the line IV-IV in FIG. 2. The femoral implant 10 includes a distal surface 16 configured for contacting the proximal surface 48 of a tibial implant 40 which is shown in FIG. 6. The femoral implant 10 may also include an apex portion 18 and support shoulders 24 to engage the prepared distal end of the femur. The apex portion 18 may be configured to be received in the cancellous bone material of the femur, whereas the supports 24 may be configured to contact the cortical bone material of the femur, so that load sharing between the cortical bone and the cancellous bone may be accomplished. The body 14 contains a transverse bore 20 which is intersected by a portion of the generally perpendicular central bore 26.

Figure 5:
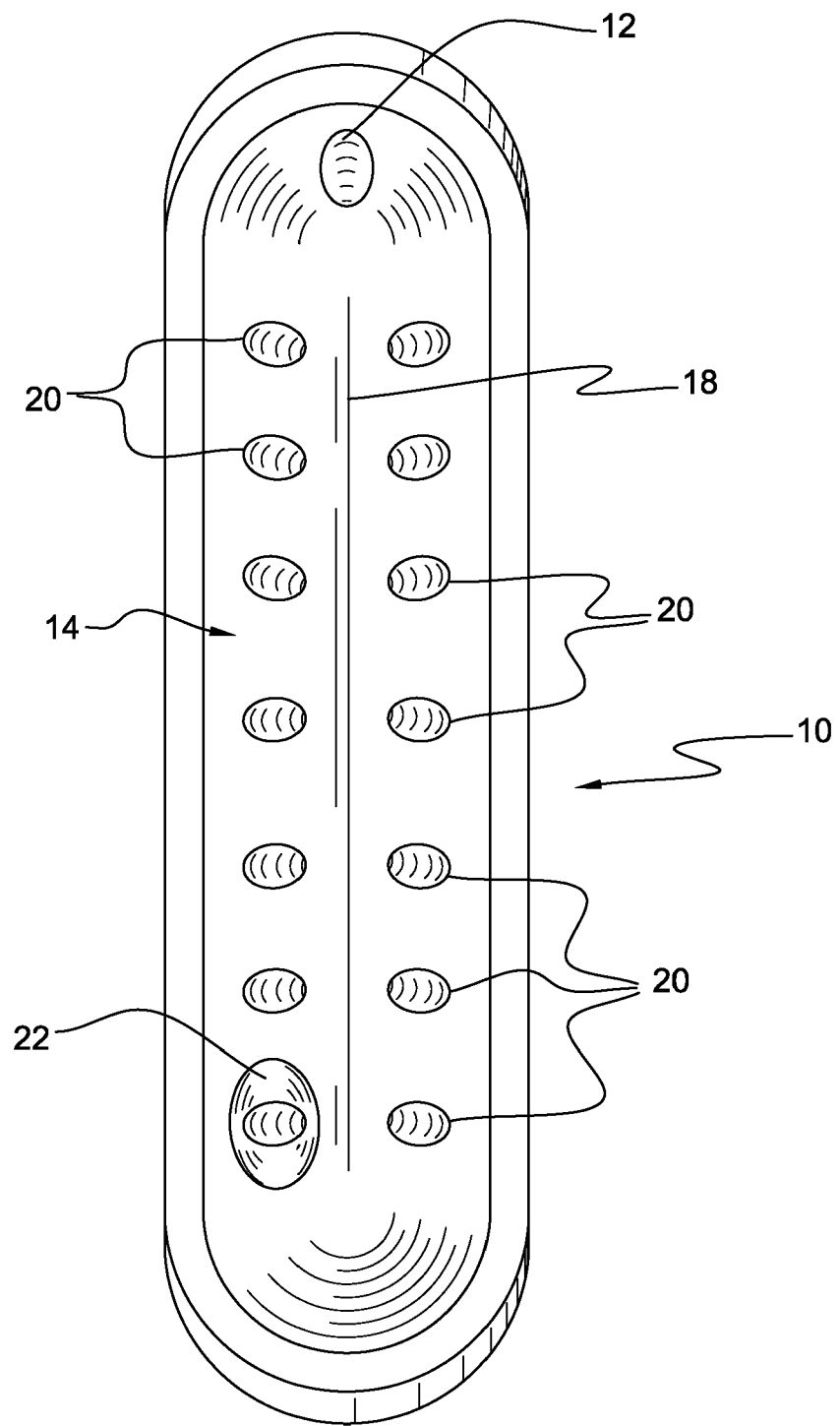
FIG. 5 is a view of the proximal surface of the femoral component of FIG. 1.

FIG. 5 shows a proximal view of the femoral component 10 illustrating the plurality of generally transverse bores or holes 20 formed through the body portion 14 substantially perpendicular to the longitudinal axis of the femoral component 10. The inner surface 22 of one transverse bore 20 may be internally threaded or otherwise adapted to receive and attach to the distal end of a fastener. A generally longitudinally oriented bore (not shown) passes through the body portion 14 of the femoral component 10 substantially perpendicular to the transverse bores 20 intersecting the transverse bores 20 causing the transverse bores 20 to be in communication with each other forming an interconnecting network of channels. The generally longitudinally oriented bore may intersect the through hole 12 causing the through hole 12 to be in communication with the interconnecting network of channels formed by the longitudinally oriented bore and the transverse bores 20.

The femoral implant 10 may be used to repair a single condyle, referred to as a unicondylar replacement. Also, two femoral implants 10 may be used in a bi-condylar replacement within the scope of the present invention.

The femoral component 10 may be shaped to reproduce the weight bearing articular surface of the knee. Moreover, it will be understood that the femoral implant 10 may be implanted without resurfacing the entire width of the condyle. Accordingly, the femoral implant 10 may form a narrow rim on the condyle which may cooperate with the remaining portion of the condyle. The femoral component 10 may be made of a high molecular weight polyethylene (HMWPE), other polymer, metal, or any other suitable material known to those skilled in the art.

Figure 7:
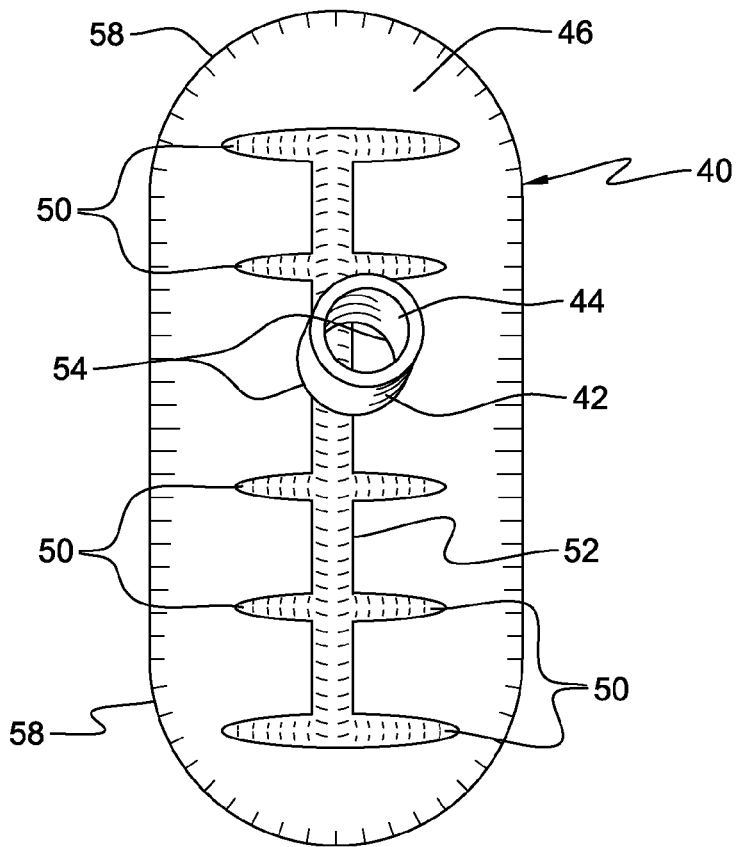
FIG. 7 is a view of the distal surface of the tibial component.

As shown in FIG. 6, the tibial implant component 40 may have a concave proximal surface 48 and a convex distal surface 46. A post 42 extends distally from the distal surface 46. The post 42 has a central bore 44 that extends to and communicates with a longitudinal groove on the distal surface of the tibial component 40 (which is shown in FIG. 7 as longitudinal groove 52). The inner surface of the central bore 44 may be internally threaded or otherwise adapted to receive and attach to the distal end of a fastener. A plurality of generally transverse grooves 50 are formed on the distal surface 46 of the tibial implant component 40. The transverse grooves 50 are substantially perpendicular to the longitudinal groove 52. The transverse grooves 50 intersect the longitudinal groove 52 resulting in the transverse grooves 50 and the longitudinal groove being in communication with each other forming an interconnecting network of grooves.

As shown in FIG. 7, a post 42 projects distally from the distal surface 46 of the tibial implant 40. The post 42 has a central bore 44 that extends to and communicates with a longitudinal groove 52 on the distal surface of the tibial component 40. The inner surface of the central bore 44 may be internally threaded or otherwise adapted to receive and attach to the distal end of a fastener. A plurality of generally transverse grooves 50 are formed on the distal surface 46 of the tibial implant component 40. The transverse grooves 50 are substantially perpendicular to the longitudinal groove 52. The transverse grooves 50 intersect the longitudinal groove 52 resulting in the transverse grooves 50 and the longitudinal groove being in communication with each other forming an interconnecting network of grooves. The post 42 has openings 54 at the base of the post where it is attached to the distal surface 46 of the tibial implant 40 to permit communication between the inner bore 44 of the post 42 to communicate with the longitudinal groove 52. The periphery 58 of the tibial component 40 is continuous, smooth and unbroken by any openings.

Figure 8:
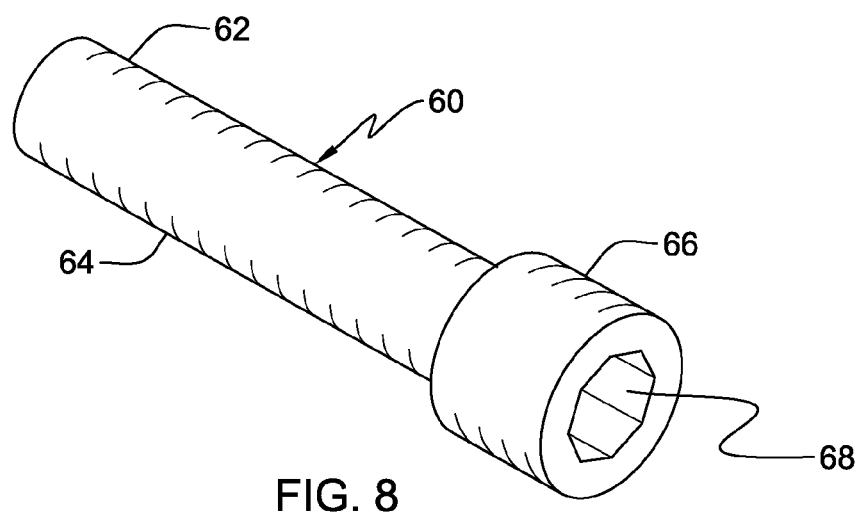
FIG. 8 is a perspective view of a fastener.

FIG. 8 is a perspective view of a screw or fastener 60 which may have a first and second portion, wherein said first portion may comprise a head portion 66 having a recessed portion 68 wherein the recessed portion may comprise a polygonal shape and a second portion, wherein said second portion 64 may comprise an elongate shaft suitable for insertion into a substrate and wherein said shaft may comprise a distal end 62 bearing external threads or other means to attach to the inner surface 22 of a transverse bore 20 of the femoral component 10 or the inner bore 44 of the post 42 of the tibial component 40. The screw or fastener 60 may be cannulated to permit the injection of bone cement into the network of bores in the femoral component 10 and the network of grooves in the tibial component 40.

Figure 9:
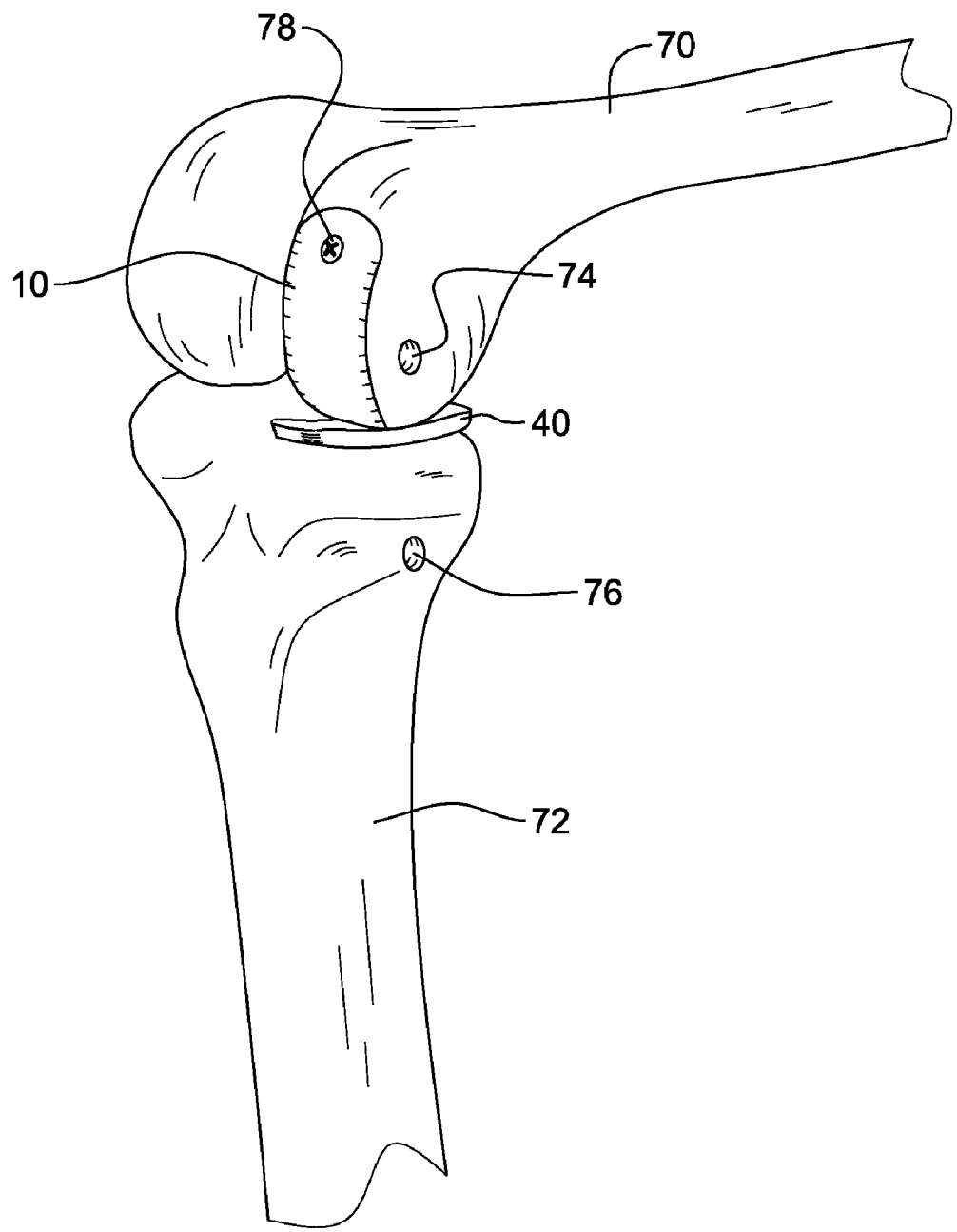
FIG. 9 is a perspective view of a knee, showing a femur and tibia, into which the femoral and tibial components have been implanted.

FIG. 9 is a perspective view of a knee, showing a femur 70 and tibia 72, into which a femoral component 10 and a tibial component 40 have been implanted. A bone screw or other fastener has been inserted into the hole in the distal surface of the femoral component 10 to secure the femoral component to the femur 70. An opening 74 of a bore for a fastener to attach to the proximal surface of the femoral component is shown on the external surface of the femur 70. An opening 76 of a bore for a fastener to attach to the distal surface of the tibial component is shown on the external surface of the tibia 72.

The tibial implant 40 may be formed of metal, polymer, or any other suitable material known to those skilled in the art.

Figure 10:
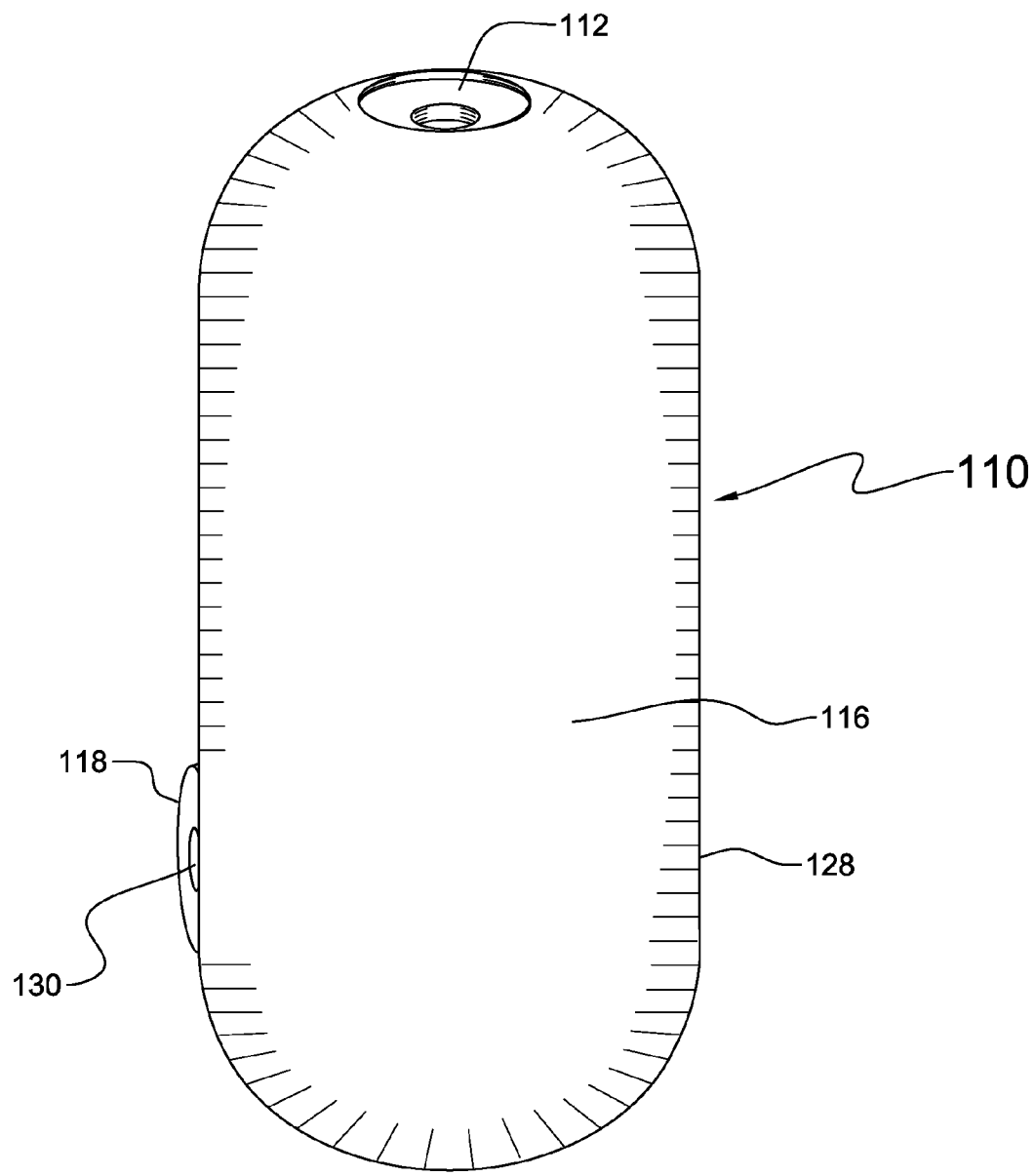
FIG. 10 is a view of the distal surface of the femoral component of the second embodiment of the femoral component.
Figure 11:
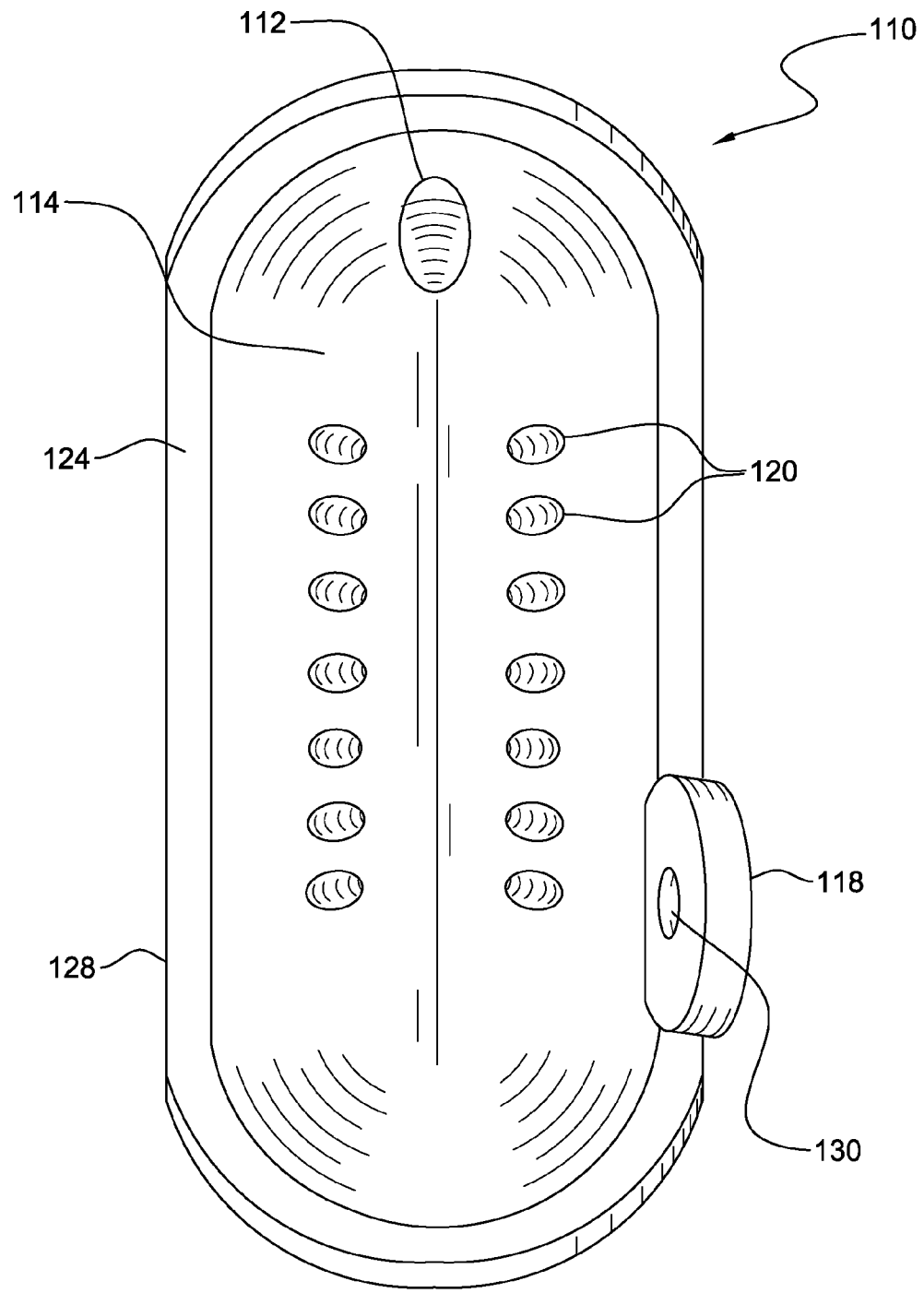
FIG. 11 is a view of the proximal surface of the second embodiment of the femoral component.

A second embodiment of the femoral component is illustrated in FIG. 10 and FIG. 11. In this second embodiment, one or more flanges 118 are added to the periphery of the femoral component illustrated in FIG. 1 through FIG. 5

A distal view of the femoral component 110 is shown in FIG. 10. The femoral component 110 may have one or more through holes 112 passing through the distal surface of 116 of the femoral component 110 for receiving a bone screw or other fastener known in the art for attaching the femoral component 110 to the distal end of a femur. The periphery 128 of the femoral component 110 is continuous, smooth and unbroken by any openings. Flange 118 is shown extending from the periphery 128 of the femoral component 110. The flange 118 may have one or more through holes 130 for receiving a bone screw or other fastener for attaching the femoral component 110 to the distal end of a femur.

FIG. 11 shows a proximal view of the femoral component 110 illustrating the plurality of generally transverse bores or holes 120 formed through the body portion 114 substantially perpendicular to the longitudinal axis of the femoral component 110. A generally longitudinally oriented bore (not shown) passes through the body portion 114 of the femoral component 110 substantially perpendicular to the transverse bores 120 intersecting the transverse bores 120 causing the transverse bores 120 to be in communication with each other forming an interconnecting network of channels. The generally longitudinally oriented bore may intersect the through hole 112 causing the through hole 112 to be in communication with the interconnecting network of channels formed by the longitudinally oriented bore and the transverse bores 120. Flange 118 is shown extending from the periphery 128 of the femoral component 110. The flange 118 may have one or more through holes 130 for receiving a bone screw or other fastener for attaching the femoral component 110 to the distal end of a femur. The distal surface of flange 118 may include a bore which passes into the longitudinal bore or into the transverse bores 120 causing the bore on the distal surface to be in communication with the interconnecting network of channels. The opening of the bore on the distal surface of flange 118 may be the opening of a through hole 130 or may be separate. The femoral implant 110 may include support shoulders 124 to engage the prepared distal end of the femur.

Figure 12:
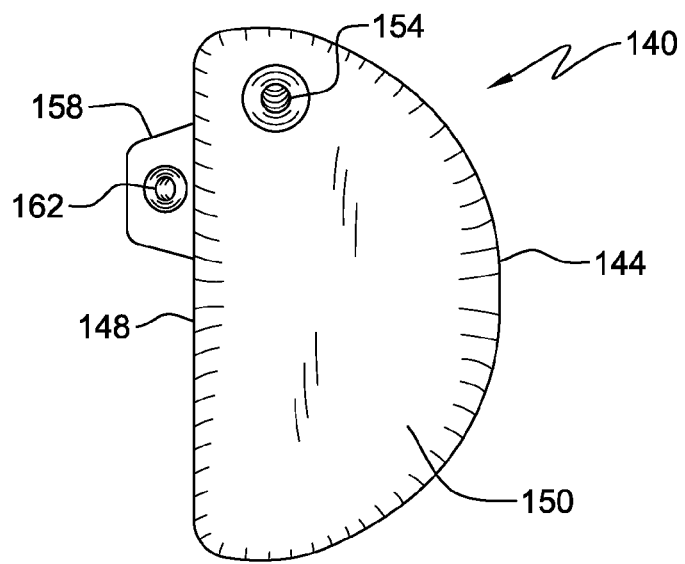
FIG. 12 is a view of the proximal surface of the second embodiment of the tibial component.

FIG. 12 is a proximal view of a second embodiment of the tibial component. The tibial component 140 when viewed from above is generally semi-circular in shape with a curved wall 144 and a generally straight wall 148. The proximal surface 150 of the tibial component is slightly concave. The tibial component 140 may have a hole 154 in the proximal surface 150 for receiving a bone screw or other fastener known in the art for attaching the tibial component 140 to the tibia. Hole 154 may pass through the tibial component 140 from the proximal surface 150 to the distal surface. Hole 154 may pass into a bore (not shown) formed within the tibial component causing the hole 154 on the proximal surface to be in communication with an interconnecting network of channels (not shown) formed within the tibial component 140.

Flange 158 may extend from the straight wall 148. The flange 158 may have a hole 162 for receiving a bone screw or other fastener for attaching the tibial component 140 to the tibia. Hole 162 may pass through the flange 158 from the proximal surface 150 to the distal surface. Hole 162 may pass into a bore (not shown) formed within the flange 158 interconnects with a network of channels (not shown) formed within the tibial component 140 causing the bore on the proximal surface to be in communication with the interconnecting network of channels.

Figure 13:
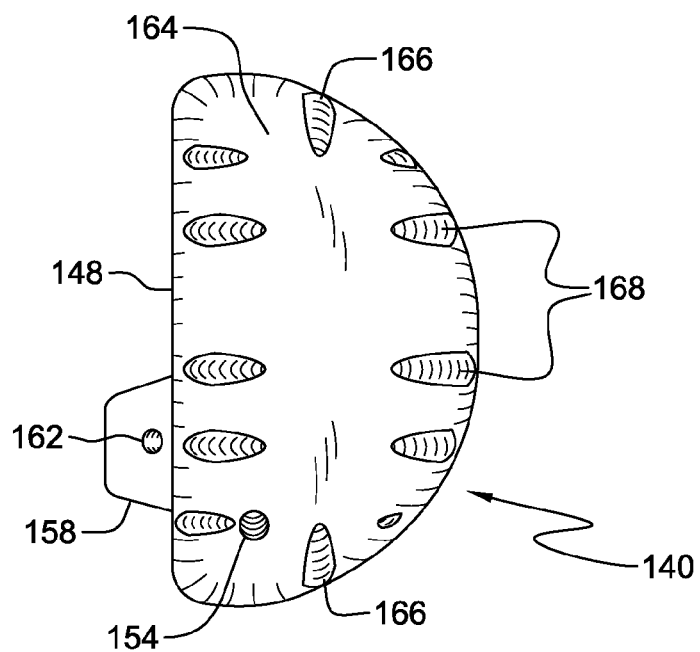
FIG. 13 is a view of the distal surface of the tibial component of FIG. 12.

FIG. 13 is a distal view of the tibial component 140 of FIG. 12. Hole 154 may pass through the tibial component 140. Flange 158 may extend from the straight wall 148. The distal surface 164 of the tibial component 140 is slightly convex. Longitudinal grooves 166 on the distal surface of the tibial component 140 are in communication with each other by a bore (not shown) which passes longitudinally through the tibial component 140. A plurality of generally transverse grooves 168 are formed on the distal surface 164 of the tibial implant component 140 are in communication with each other by transverse bores (not shown) which pass transversely through the tibial component 140. The transverse grooves 168 are substantially perpendicular to the longitudinal grooves 166. The transverse bores intersect the longitudinal bore resulting in interconnecting network of bores.

In the preferred embodiment of the invention, the body of the femoral component possesses a network of bores which is in communication with a bore on the distal surface of the component. The cannulation permits bone cement to be injected into the network of bores and into the interface between the proximal surface of the femoral component and the prepared distal surface of the femur after the femoral component has been implanted. Following injection of the bone cement, the opening on the distal surface may be sealed by inserting an appropriately sized bone screw or other fastener through the opening into the femur or by placing a cap or plug into the opening.

The tibial component possesses a network of grooves formed upon its distal surface which is in communication with a network of bores formed within the body of the tibial component. The network of bores is in communication with an opening on the proximal surface of the tibial component. The opening on the proximal surface of the tibial component permits bone cement to be injected through the network of bores into the network of grooves which are formed within the distal surface of the tibial component and into the interface between the distal surface of the tibial component and the proximal surface of the prepared tibial after the tibial component has been implanted. Following injection of the bone cement, the opening on the proximal surface may be sealed by inserting an appropriately sized bone screw or other fastener through the opening into the tibia or by placing a cap or plug into the opening.

It is to be understood that various changes in the details, materials, steps, and arrangements of parts, which have been herein described and illustrated in order to describe the nature of the knee joint prosthesis, may be made by those skilled in the art within the principle and scope of the invention. Numerous modifications and alternative arrangements may be devised by those skilled in the art without departing from the spirit and scope of the present invention. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A femoral condyle resurfacing prosthesis comprising:
a curved body having a convex distal surface, a concave proximal surface, and a longitudinal apex portion projecting from the proximal surface;
a plurality of transverse holes directed through the body;
a longitudinal bore directed along the body, the longitudinal bore intersecting the plurality of transverse holes providing a network for distributing bone cement; and
a flange mounted to the concave proximal surface of the body;
wherein, when mounted to a femur, the distal surface of the prosthesis is positioned to bear against a surface of a tibial condyle.

2. The prosthesis as recited in claim 1, wherein the prosthesis comprises a partial femoral condylar replacement prosthesis.

3. The prosthesis as recited in claim 2, wherein the partial femoral condylar replacement prosthesis comprises a narrow rim adapted to cooperate with a remaining surface portion of a femoral condyle.

4. The prosthesis as recited in claim 1, wherein the flange includes an axis of elongation, and wherein the axis of elongation extends substantially perpendicular to the concave proximal surface of the body.

5. The prosthesis as recited in claim 1, wherein the prosthesis comprises a unicondylar replacement prosthesis.

6. The prosthesis as recited in claim 1, wherein the curved body comprises a periphery, and wherein the periphery of the curved body is continuous and smooth.

7. The prosthesis as recited in claim 6, wherein the periphery of the curved body is unbroken by an openings.

8. The prosthesis as recited in claim 1, wherein the plurality of transverse holes are directed substantially perpendicular to a longitudinal axis of the body.

9. The prosthesis as recited in claim 1, wherein the longitudinal bore is directed substantially perpendicular to the plurality of transverse holes.

10. The prosthesis as recited in claim 1, further comprising a hole in the concave distal surface, the hole communicating with the longitudinal bore.

11. The prosthesis as recited in claim 1, wherein the flange extends from a periphery of the body.

12. The prosthesis as recited in claim 1, wherein the flange includes a bore adapted to receive a fastener.

13. The prosthesis as recited in claim 1, wherein the flange includes a bore in communication with the network for distributing bone cement.

14. The prosthesis as recited in claim 1, wherein the concave proximal surface comprises support shoulders adapted to engage the femur.

15. The prosthesis as recited in claim 14, wherein the flange comprises a cylindrical projection from one of the support shoulders of the body.

16. A tibial condyle resurfacing prosthesis comprising:
a body having a concave proximal surface and a convex distal surface;
a plurality of grooves in the distal surface, the plurality of grooves communicating with a plurality of transverse holes directed through the body;
a longitudinal bore directed through the body, the longitudinal bore intersecting the plurality of transverse holes providing a network for distributing bone cement; and
a flange extending from a lateral wall of the body;
wherein, when mounted to a tibia, the proximal surface of the prosthesis is positioned to bear against a surface of a femoral condyle.

17. The prosthesis as recited in claim 16, wherein the prosthesis comprises a partial tibial condylar replacement prosthesis.

18. The prosthesis as recited in claim 16, wherein the flange includes an axis of elongation, and wherein the axis of elongation extends substantially perpendicular to the lateral wall of the body.

19. The prosthesis as recited in claim 16, wherein the prosthesis comprises a unicondylar replacement prosthesis.

20. The prosthesis as recited in claim 16, wherein the lateral wall comprises a substantially straight wall, and wherein the body further comprises a curved wall opposite the lateral wall.

21. The prosthesis as recited in claim 16, wherein the plurality of transverse holes are directed substantially perpendicular to a longitudinal axis of the body.

22. The prosthesis as recited in claim 16, wherein at least some of the plurality grooves comprise longitudinal grooves which communicate with the longitudinal bore.

23. The prosthesis as recited in claim 16, further comprising a hole in the convex proximal surface, the hole communicating with the longitudinal bore.

24. The prosthesis as recited in claim 16, wherein the flange includes a hole adapted to receive a fastener.

25. The prosthesis as recited in claim 16, wherein the flange includes a bore in communication with the network for distributing bone cement.

26. The prosthesis as recited in claim 16, wherein the flange comprises a rectangular projection from a lateral wall of the body.

* * * * *